United States Patent [19]
Minton et al.

[11] Patent Number: 5,462,166
[45] Date of Patent: Oct. 31, 1995

[54] PACKAGE SEAL FOR INDIVIDUALLY PACKAGED SANITARY NAPKINS

[75] Inventors: Gerald T. Minton, Greenville, N.C.; Lisa J. Horwich, Cincinnati; Steven R. Gilbert, Fairfield, both of Ohio

[73] Assignee: The Procter & Gamble Company, Cincinnati, Ohio

[21] Appl. No.: 194,891

[22] Filed: Feb. 14, 1994

[51] Int. Cl.⁶ ................................................. A61F 13/20
[52] U.S. Cl. ...................... 206/440; 206/494; 229/87.05
[58] Field of Search .................................. 428/102, 103; 206/438, 440, 278, 494, 812; 229/87.05

[56] References Cited

U.S. PATENT DOCUMENTS

| | | | |
|---|---|---|---|
| 3,511,746 | 5/1970 | Davies | 161/147 |
| 3,937,395 | 2/1976 | Lawes | 229/62.5 |
| 4,324,823 | 4/1982 | Ray, III | 428/43 |
| 4,379,192 | 4/1983 | Wahlquist et al. | 428/156 |
| 4,470,153 | 9/1984 | Kenan | 383/100 |
| 4,540,089 | 9/1985 | Maloney | 206/219 |
| 4,556,146 | 12/1985 | Swanson et al. | 206/440 |
| 4,566,927 | 1/1986 | Wood | 156/203 |
| 4,706,298 | 11/1987 | Lipes et al. | 383/71 |
| 4,743,123 | 5/1988 | Legters et al. | 383/103 |
| 4,834,554 | 5/1989 | Stetler, Jr. et al. | 383/100 |
| 4,854,984 | 8/1989 | Ball et al. | 156/73.5 |
| 4,917,675 | 4/1990 | Taylor et al. | 206/440 X |
| 4,966,286 | 10/1990 | Muckenfuhs | 206/494 X |
| 4,998,620 | 3/1991 | Taylor | 206/812 X |
| 5,061,500 | 10/1991 | Mendenhall | 426/118 |
| 5,181,610 | 1/1993 | Quick et al. | 206/447 |
| 5,242,057 | 9/1993 | Cook et al. | 206/494 X |
| 5,334,643 | 8/1994 | Gage | 524/232 |

FOREIGN PATENT DOCUMENTS

WO94/14396  7/1994  WIPO.

OTHER PUBLICATIONS

Report titled "Preliminary Report on the Effect of Shapes and Patterns on the Strength Characteristics of Bonded Laminar Sheets," prepared by Frederick Chen (as supervised by Dr. Max Brown, University of Cincinnati) Mar. 24, 1988.

Primary Examiner—Jacob K. Ackun
Attorney, Agent, or Firm—Gerry S. Gressel; Jeffrey V. Bamber; Larry L. Huston

[57] ABSTRACT

The present invention provides a sanitary napkin enclosed within a flexible wrapper formed of thermoplastic film. The sanitary napkin and wrapper are folded as a unit about at least two lateral fold axes, so that the sanitary napkin is disposed between two or more layers of the wrapper. The layers of the folded wrapper are joined by a pair of laterally spaced apart releasable seals. Each releasable seal extends longitudinally along a longitudinal edge of the wrapper. Each releasable seal comprises an array of discrete thermal-mechanical bonds joining the layers of the wrapper. The array of discrete bonds extends in a first direction generally parallel to a package edge and in a second direction generally perpendicular to the package edge. This arrangement of ratios of bond width to bond spacing reduces the strength of the seal parallel to the package edge relative to the strength of the seal perpendicular to the package edge. The seal arrangement thereby enhances the ability of the seal to resist bursting in a direction perpendicular to the package edge, while permitting the package edge to be peeled apart in a direction generally parallel to the package edge.

26 Claims, 3 Drawing Sheets

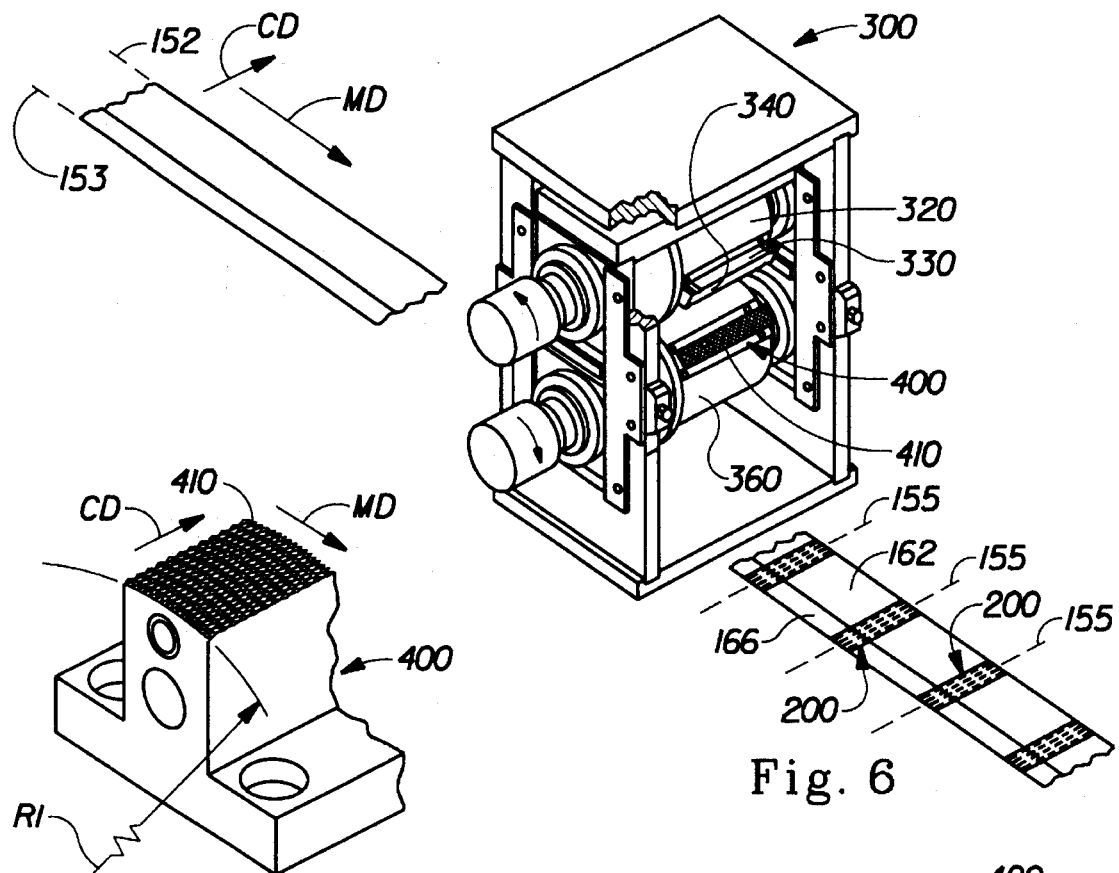

PACKAGE SEAL FOR INDIVIDUALLY PACKAGED SANITARY NAPKINS

FIELD OF THE INVENTION

The present invention relates to individually packaged disposable absorbent articles such as sanitary napkins, and more particularly, to improved releasable seals for individually packaged sanitary napkins.

BACKGROUND OF THE INVENTION

Individually packaged disposable absorbent articles, such as individually packaged sanitary napkins, are known in the art. Individually packaged sanitary napkins provide the advantage that they are compact (e.g., they can be conveniently carried in a consumer's pocket or purse). Individually packaged sanitary napkins also resist soiling of the sanitary napkin prior to use, while the sanitary napkin is being carried by the consumer. U.S. Pat. No. 4,556,146 issued Dec. 3, 1985 to Swanson et al. discloses an individually packaged disposable absorbent article having an absorbent pad and a protective wrapper. The absorbent pad and wrapper are folded as unit about two fold-axes, and longitudinal flaps of the wrapper are frangibly sealed, such as by heat sealing.

U.S. Pat. No. 5,181,610 issued Jan. 26, 1993 to Quick et al. discloses a pouch for packaging sanitary napkins. The side seams of the pouch are formed by the application of heat in combination with mechanical deformation of two or more layers of the pouch. Embossing plates having different embossing patterns including a dot pattern, a parallel line pattern, and a criss-crossed line pattern are disclosed. Quick et al. discloses that the pouch side seams can be made so that the pouch is opened by peeling apart the seams, or so that the seams are sealed so tightly that the pouch can be opened only by tearing the pouch material.

While the prior art provides seals for individually wrapped sanitary napkins, the Applicants of the present invention have recognized that known seals have inherent disadvantages, especially when individually wrapped sanitary napkins are produced on high speed production lines. During assembly and packaging on high speed production lines, the individually wrapped sanitary napkins can be compressed. Such compression can cause air trapped within wrapper to "blow out" the seals along the edge of the wrapper. "Blown" seals are undesirable because they permit contamination of the sanitary napkin within the wrapper, and present a low quality appearance to the consumer.

Blown seals can be prevented by uniformly increasing the seal strength. Unfortunately, uniformly increasing seal strength is not an acceptable solution. High seal strength can cause the wrapper edges to tear on opening, rather than smoothly peeling apart. Tearing of the wrapper edge is not consumer preferred because tearing of the wrapper edge is relatively difficult, noisy, and indiscreet. Torn wrapper edges also present a low quality appearance to the consumer. As a result, manufacturers of individually packaged sanitary napkins have been forced to trade off between relatively low strength wrapper seals which can open prematurely and permit contamination of the sanitary napkin prior to use, and relatively high strength wrapper seals which require tearing of the wrapper.

Accordingly, it is an object of the present invention to provide an individually packaged disposable absorbent article having a releasable package seal.

It is another object of the present invention to provide an individually packaged disposable absorbent article having a releasable package seal which permits peeling of the seal, without tearing, in the direction parallel to the edge of the package and resists bursting of the package seal in the direction perpendicular to the edge of the package.

A further object of the present invention is to provide an individually packaged disposable absorbent article comprising a package having thermoplastic film layers joined at a releasable seal along an edge of the package, the releasable seal comprising an array of discrete thermal-mechanical bonds, and the seal having a ratio of the bond width to bond spacing as measured in a direction perpendicular to the package edge which is less than the ratio of bond width to bond spacing as measured in a direction parallel to the package edge.

SUMMARY OF THE INVENTION

The present invention provides a flexible package having two or more thermoplastic layers joined at a releasable seal along at least one edge of the package. A preferred embodiment of the invention is an individually packaged disposable absorbent article, such as a sanitary napkin enclosed within a flexible wrapper formed of thermoplastic film. The sanitary napkin and wrapper are folded as a unit about at least two lateral fold axes, so that the sanitary napkin is disposed between two or more layers of the wrapper. The layers of the folded wrapper are joined by a pair of laterally spaced apart releasable seals.

Each releasable seal extends longitudinally along a longitudinal edge of the wrapper.

Each releasable seal comprises an array of bonds joining the layers of the wrapper. The array of bonds preferably comprises an array of discrete, thermal-mechanical bonds. The array of discrete thermal-mechanical bonds extends in a first direction generally parallel to a package edge and in a second direction generally perpendicular to the package edge. The ratio of bond width to bond spacing in a direction generally perpendicular to the package edge is less than the ratio of bond width to bond spacing in a direction generally parallel to the package edge. This arrangement of ratios of bond width to bond spacing reduces the strength of the seal parallel to the package edge relative to the strength of the seal perpendicular to the package edge. The seal arrangement thereby enhances the ability of the seal to resist bursting in the direction perpendicular to the package edge, while permitting the package edge to be peeled apart, without tearing, in the direction generally parallel to the package edge.

The spacing between adjacent bonds in the direction generally perpendicular to the package edge is preferably greater than the spacing between adjacent bonds in the direction generally parallel to the package edge. The spacing between adjacent bonds in the direction generally perpendicular to the package edge can also be greater than the bond width as measured in a direction generally perpendicular to the package edge, to further enhance the ease of opening the package along a direction parallel to the package edge. In one embodiment the discrete bonds are arranged in rows extending generally parallel to the package edge and in columns extending generally perpendicular to the package edge, with the spacing between adjacent rows greater than the spacing between adjacent columns. The releasable seal preferably has a bonded area ratio of no more than about twenty percent to provide a peelable seal, where the bonded area ratio is a measure of the ratio of seal bonded area to seal unbonded area.

DESCRIPTION OF THE DRAWINGS

While the Specification concludes with claims particularly pointing out and distinctly claiming the present invention, the invention will be better understood from the following description taken in conjunction with the accompanying drawings in which like designations are used to designate substantially identical elements, and in which:

FIG. 6 is a perspective view of a portion of a sanitary napkin converting line showing a crimping assembly for forming individually packaged sanitary napkins.

FIG. 7 is a partial perspective view of a crimping die which can be used in the crimping assembly of FIG. 6.

FIG. 8 is a plan view of a crimping die used to provide a releasable seal according to one embodiment of the present invention, showing the arrangement of truncated pyramids forming the die surface.

FIG. 9 is a cross-sectional schematic view of the crimping die of FIG. 8 taken along line 9—9 in FIG. 8.

FIG. 10 is a cross-sectional schematic view of the crimping die of FIG. 8 taken along line 10—10 in FIG. 8.

DETAILED DESCRIPTION

As used herein the term "absorbent article" refers to devices which absorb and contain body exudates, and more specifically, refers to devices which are placed against or in proximity to the body of the wearer to absorb and contain the various exudates discharged from the body. Such absorbent articles include, but are not limited to, sanitary napkins, incontinence pads, diapers, training pants, and training briefs. The term "disposable" is used herein to describe absorbent articles which are not intended to be laundered or otherwise restored or reused as an absorbent article.

Figure 1:
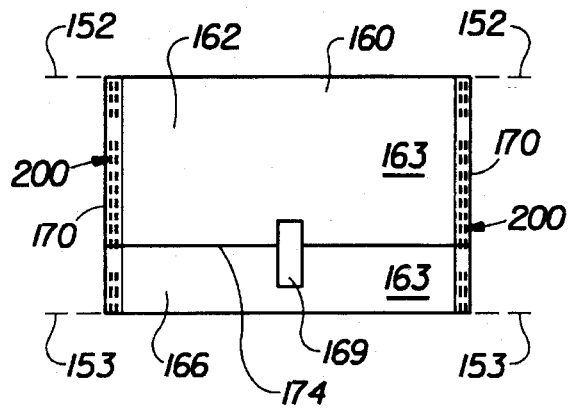
FIG. 1 is a schematic frontal view of an individually packaged disposable absorbent article, such as a sanitary napkin enclosed in a flexible wrapper, the flexible wrapper and the sanitary napkin folded as unit about two spaced apart lateral fold axes to enclose the sanitary napkin within the flexible wrapper, and each longitudinal edge of the wrapper having a releasable seal.
Figure 2:
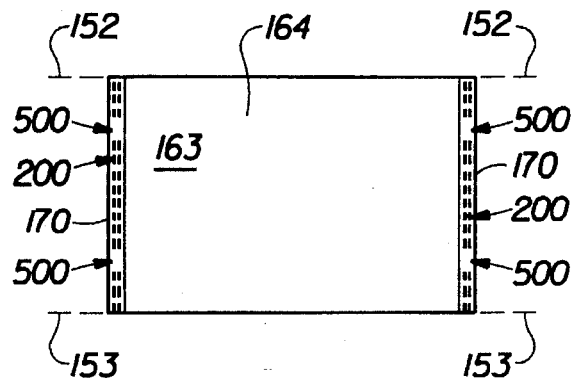
FIG. 2 is a schematic rearward view of the individually packaged disposable absorbent article shown in FIG. 1.
Figure 3:
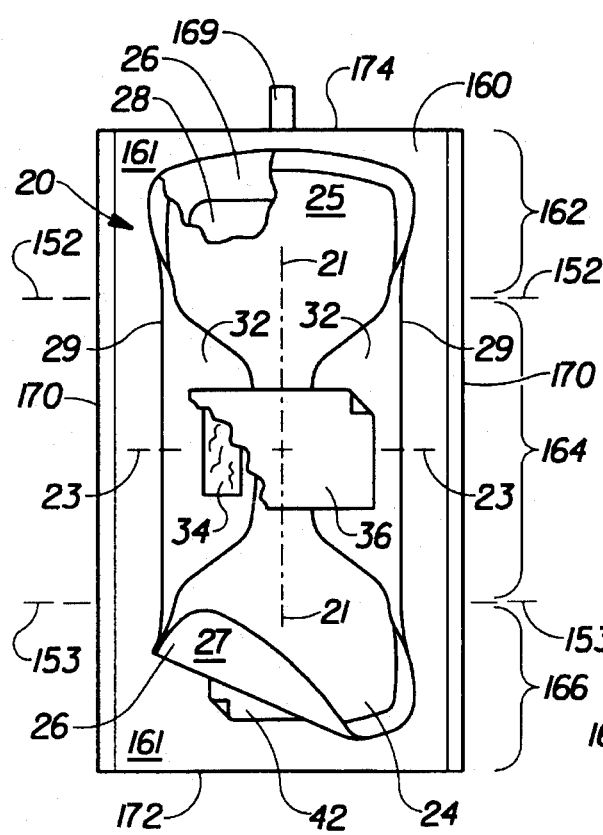
FIG. 3 is a schematic view of a portion of the individually packaged sanitary napkin of FIG. 1 wherein the releasable seals have been peeled apart and the sanitary napkin and the flexible wrapper are shown unfolded about the two lateral fold axes.

FIGS. 1 through 3 show an individually packaged disposable absorbent article comprising a sanitary napkin 20 packaged in a flexible package, such as a flexible wrapper 160. FIGS. 1 and 2 are front and rear views showing the flexible wrapper 160 folded and sealed to enclose the sanitary napkin 20. The sanitary napkin 20 is not visible in FIGS. 1 and 2. In FIG. 3, the flexible wrapper 160 is unfolded to reveal the sanitary napkin 20.

Referring to FIG. 3, the sanitary napkin 20 has a longitudinal centerline 21 and a lateral centerline 23. The term "longitudinal," as used herein, refers to a line, axis, or direction in the plane of the sanitary napkin 20 that is generally aligned with (e.g., approximately parallel to) a vertical plane which bisects a standing wearer into left and right body halves when the sanitary napkin 20 is worn. The term "lateral" as used herein refers to a line, axis, or direction which lies within the plane of the sanitary napkin 20 and which is generally perpendicular to the longitudinal direction.

The sanitary napkin 20 preferably comprises a liquid pervious topsheet 24 having a body facing surface 25, a liquid impervious backsheet 26 joined with the topsheet 24 and having a garment facing surface 27, and an absorbent core 28 positioned intermediate the topsheet 24 and the backsheet 26. The sanitary napkin 20 can also include a pair of flaps 32 having flap adhesive 34. The flaps 32 are configured to drape over the edges of the wearer's panties and can be folded back under the panty and attached to the garment facing side of the panty with the flap adhesive 34. When the sanitary napkin 20 is enclosed within the wrapper 160, the flaps 32 can be secured in a folded position over the topsheet 22 by a piece of flap release paper 36. The sanitary napkin 20 has a longitudinally extending perimeter 29 indicated in FIG. 3. The following U.S. Patents are incorporated herein by reference for the purpose of showing preferred sanitary napkin constructions and components: U.S. Pat. No. 4,950,264 issued Aug. 21, 1990 to Osborn; U.S. Pat. No. 4,589,87 issued May 20, 1986 to Van Tilburg; and U.S. Pat. No. 5,007,906 issued Apr. 16, 1991 to Osborn et al.

The flexible wrapper 160 has an interior surface 161 and an exterior surface 163. The sanitary napkin 20 includes garment attachment adhesive (not shown) for joining the garment facing surface 27 of the backsheet 26 to the wearer's panties. A strip of release paper 42 covers the garment attachment adhesive until the wearer is ready to fasten the sanitary napkin to the undergarment. One surface of the strip of release paper 42 is joined to the garment facing surface 27 of backsheet 26 by the garment attachment adhesive, and an opposite surface of the strip of release paper 42 is joined to the interior surface 161 of the flexible wrapper 160 by wrapper adhesive (not shown).

The flexible wrapper 160 protects the sanitary napkin 20 from becoming soiled prior to use. By "flexible" it is meant that the wrapper 160 can be nondestructively deformed, such as by folding, twisting, or bunching, as occurs when carried in a consumer's purse or pocket. The sanitary napkin 20 is folded as a unit with the flexible wrapper 160 along two longitudinally spaced apart and laterally extending fold axes 152 and 153. The fold axes 152 and 153 divide the flexible wrapper 160 into three panels 162, 164, and 166. The panels 162, 164, 166 form three wrapper layers when the flexible wrapper is folded along the fold axes 152 and 153. At least a portion of the sanitary napkin 20 is disposed between the panels 164 and 166. The panel 162 is folded so that a portion of the panel 162 forms a closure flap overlying the panel 166. The closure flap portion of the panel 162 can be adhesively joined to the underlying panel 166, such as by a piece of tape 169 comprising pressure sensitive adhesive.

The wrapper 160 and sanitary napkin 20 are shown in a closed, folded configuration in FIGS. 1 and 2. FIG. 3 shows the wrapper 160 and sanitary napkin 20 unfolded along the two fold axes 152 and 153. The flexible wrapper 160 has a pair of laterally spaced apart and longitudinally extending edges 170 which are disposed laterally outward of the perimeter 29 of the sanitary napkin 20. The flexible wrapper 160 also has a first laterally extending free end 172 associated with the panel 166 and a second laterally extending free end 174 associated with the panel 162. The sanitary napkin can be joined to the flexible wrapper 160 so that the longitudinal centerline 21 of the sanitary napkin is generally parallel to the edges 170 and the lateral centerline 23 of the sanitary napkin is generally perpendicular to the edges 170 when the wrapper 160 and the sanitary napkin 20 are unfolded as shown in FIG. 3.

The flexible wrapper 160 can be formed from various materials, and is preferably water impervious to protect the sanitary napkin from moisture. A preferred flexible wrapper 160 is formed from a thermoplastic film. The term "thermoplastic film" refers to polymeric films such as polyolefinic films, layers of which can be softened and fused together by the application of heat and pressure. A suitable material from which the flexible wrapper 160 can be formed comprises a polyethylene film having a thickness of about 0.025 millimeter (about 0.001 inch).

The folded wrapper 160 has a releasable seal 200 along each of the wrapper edges 170. The releasable seal 200 joins the adjacent panels of the flexible wrapper 160 together along the edges 170 to prevent dirt or other contaminants from entering the folded wrapper 160 between the individual panels 162, 164, and 166. The term "releasable seal" refers to a non-permanent, non-refastenable joining of two or more of the panels 162, 164, and 166. The releasable seal 200 can join the panels 162 and 164 in a top portion of the wrapper 160 adjacent the fold axis 152, and join the panels 166 and 164 in a bottom portion of the wrapper 160 adjacent fold axis 153. In a central portion of the wrapper 160 where the panel 162 overlies the panel 166, and the panel 166 overlies the panel 164, the releasable seals 200 can join all three panels 162, 164, and 166 along the edges 170. To open the wrapper 160, the free end 174 associated with the panel 162 is grasped by the consumer and lifted away from the underlying panel 166, thereby peeling apart the releasable seals 200 along a direction generally parallel to the edges 170.

Individually packaged sanitary napkins can be produced on a high speed assembly line by first assembling the individual components of the sanitary napkin 20. The sanitary napkins 20, each having a strip of release paper 42, can then be joined at spaced apart locations to a continuous web of flexible wrapper material. The web of wrapper material and the sanitary napkins can then be folded as a unit about the two axes 152 and 153. The folded web enclosing the spaced apart sanitary napkins can then be directed through a sealing apparatus 300 as shown in FIG. 6 to form the releasable seals 200.

The sealing apparatus 300 includes an anvil roll 320 and a die roll 360. The anvil and die rolls 320, 360 rotate in the direction indicated by the arrows in FIG. 6. The anvil roll 320 carries four anvils 330 (only one shown in FIG. 6) spaced at equal intervals of about 90 degrees around the circumference of the anvil roll 320. Each anvil 330 has a generally smooth surface 340. The die roll 360 carries four dies 400 (only one shown in FIG. 6) spaced at equal intervals of about 90 degrees around the circumference of the anvil roll 360. Each die 400 has a patterned impression surface 410. The anvil surfaces 340 and the die surfaces 410 are heated, and the anvil and die rolls 320 and 360 are supported to provide a predetermined interference between opposed anvil and die surfaces 340 and 410 as the rolls 320 and 360 rotate. A suitable sealing apparatus 300 is an end seal unit manufactured by the Curt G. Joa Company of Sheboygan Falls, Wis.

After the sanitary napkins 20 are joined to the web of wrapper material at spaced apart locations along the length of the web, the web of wrapper material and the sanitary napkins 20 are folded as a unit about the axes 152 and 153, and then carried through the sealing apparatus 300 in the machine direction (MD), as shown in FIG. 6. The axes 152 and 153 are generally parallel to the machine direction, and generally perpendicular to the cross machine direction (CD). Spaced apart portions of adjacent panels 162, 164 and 166 located between adjacent sanitary napkins 20 are joined together by the application of heat and pressure as those portions of the adjacent panels pass between opposed anvil and die surfaces 340 and 410. The continuous web of wrapper material is then cut along axes 155, which are generally parallel to the cross machine direction, to provide individually packaged sanitary napkins having a releasable seal 200 along each edge 170.

During subsequent assembly and packaging, the individually wrapped sanitary napkins can be compressed. Such compression can cause air trapped within wrapper 160 to rupture the releasable seals 200 along the edges 170 of the individually wrapped sanitary napkins. Broken seals are undesirable because they can permit contamination of the sanitary napkin 20 within the flexible wrapper 160, and because they present a low quality appearance to the consumer. Broken seals can be prevented by uniformly increasing the seal strength. Unfortunately, uniformly increasing seal strengths is not an acceptable solution. High seal strengths can cause the flexible wrapper 160 to tear upon opening. Tearing of the wrapper edge 170 is not desirable because tearing of the wrapper edge 170 is relatively difficult, noisy, and indiscreet. It is desirable that the releasable seal 200 be opened by smoothly peeling apart the joined panels 162, 164, and 166, yet resist rupturing due to compressive loads.

Figure 4:
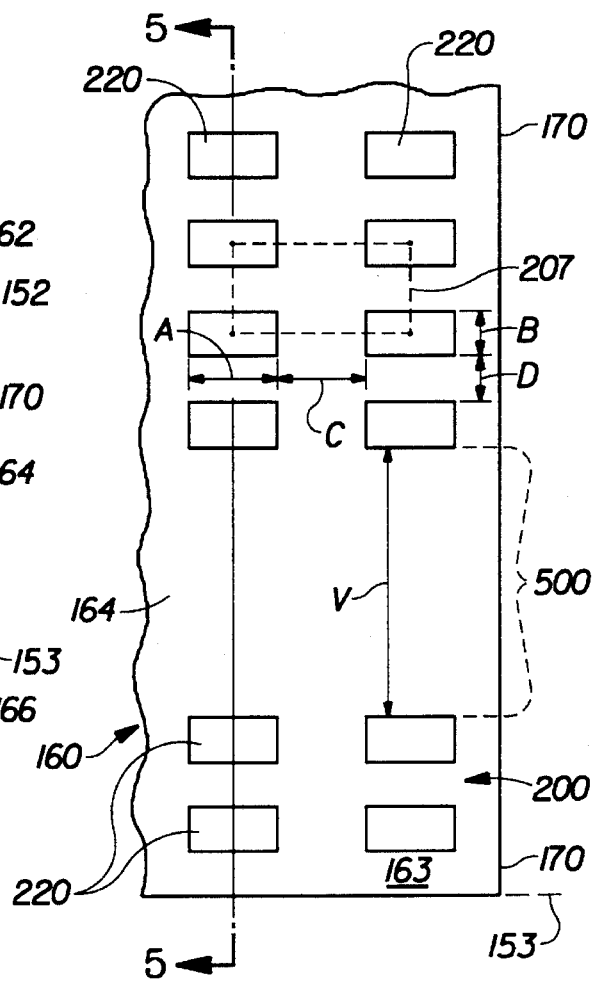
FIG. 4 is a schematic view of an array of discrete bonds according to one embodiment of the present invention, wherein the discrete bonds are arranged in rows parallel to the package edge and columns generally perpendicular to the package edge, and wherein the releasable seal formed by the array of discrete bonds is interrupted by a vent passage.

FIG. 4 shows a portion of an individually packaged sanitary napkin having a releasable seal 200 according to one embodiment of the present invention. The releasable seal 200 preferably comprises an array of discrete thermal-mechanical bonds 220. The term "thermal-mechanical bond" refers to a bond formed by softening and fusing together two or more layers of the wrapper 160 by the application of heat and pressure. The array of discrete thermal bonds 220 extends in a first direction generally parallel to the edge 170 and in a second direction generally perpendicular to the edge 170. In FIG. 4 the array of discrete bonds 220 comprises a plurality of rows and columns of generally rectangular shaped discrete bonds 220. Each row of discrete bonds 220 extends generally parallel to the edge 170 (two rows shown in FIG. 4) and each column of discrete bonds 220 extends generally perpendicular to the edge 170 (six columns shown in FIG. 4).

The array of discrete bonds 220 comprises at least two rows, and preferably at least three rows of discrete bonds 220 extending generally parallel to the edge 170. It is desirable to have a plurality of rows of bonds 220 so that if the bonds in one row are inadvertently broken, the bonds in the remaining rows will prevent contamination of the sanitary napkin 20.

The discrete bonds 220 are sized and spaced to provide a ratio of bond width to bond spacing in a direction generally perpendicular to the edge 170 which is less than the ratio of bond width to bond spacing in a direction generally parallel to the edge 170. The term bond width refers to continuous, uninterrupted bond width. For example, the bond width associated with a solid circular shaped bond would be the diameter of the bond, while the bond width associated with a ring shaped bond would be the width of the rim of the ring.

Without being limited by theory, it is believed that this arrangement of discrete bonds 220 increases the strength of the releasable seal 200 in a direction perpendicular to the edge 170 relative to the strength of the releasable seal 200 in a direction parallel to the edge 170. This arrangement of discrete bonds 220 can therefore provide a releasable seal 200 that is peelable in a direction parallel to the edge 170, yet resists rupture of the releasable seal 200 by forces acting generally perpendicular to the edge 170 (e.g. forces caused by the compression of air trapped within the flexible wrapper 160).

Referring to FIG. 4, the ratio of bond width to bond spacing in a direction generally perpendicular to the edge 170 is the width A of the discrete bonds 220 divided by the spacing C between discrete bonds 220 (A/C), where the width A and the spacing C are measured along a direction generally perpendicular to the edge 170. The ratio of the bond width to bond spacing in a direction generally parallel to the edge 170 is the width B of the discrete bonds 220 divided by the spacing D between discrete bonds 220 (B/D), where the width B and the spacing D are measured along a direction generally parallel to the edge 170. The ratio of bond width to bond spacing in a direction generally perpendicular to the edge 170 is preferably less than 0.9 times, and more preferably less than 0.85 times the ratio of bond width to bond spacing in a direction generally parallel to the edge 170 to reduce the strength of the releasable seal 200 in a direction parallel to the edge 170 relative to the strength of the releasable seal in a direction perpendicular to the edge 170.

Figure 12:
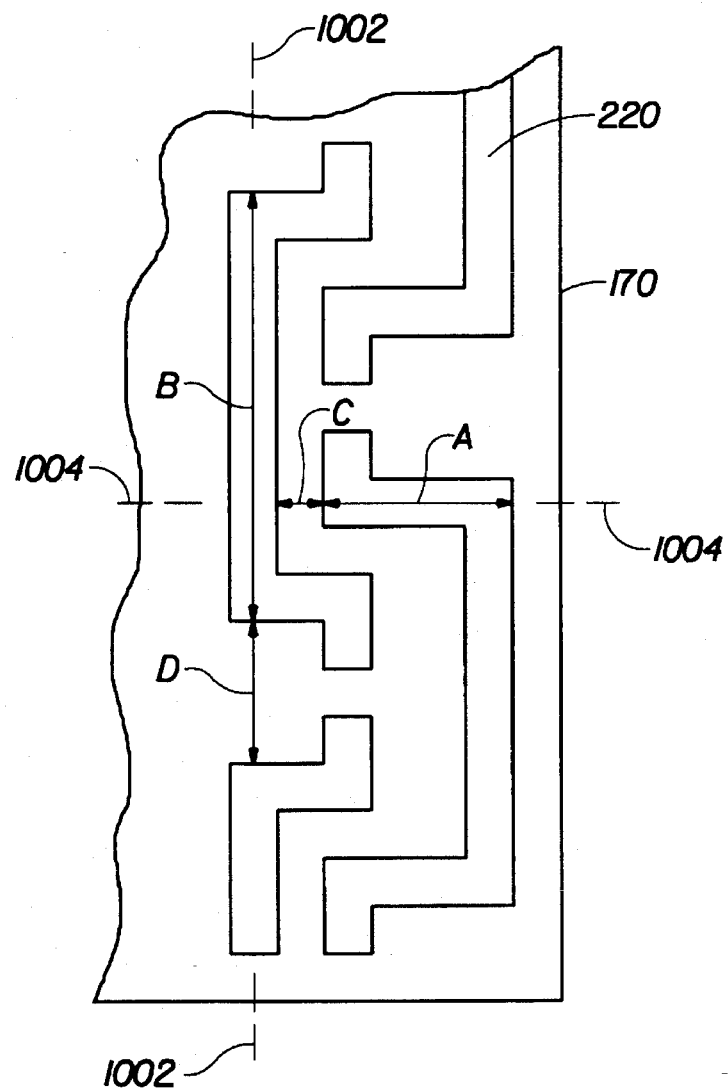
FIG. 12 is a schematic view of an array of discrete bonds having varying bond widths and bond spacing.

In FIG. 4, the bond widths and bond spacings are generally uniform (with the exception of a vent 500, which is discussed below). FIG. 12 shows an array of bonds 220 having bond widths and bond spacings that vary along directions parallel to and perpendicular to the edge 170. If the bond width or the bond spacing vary along a direction perpendicular to the edge 170, the ratio of bond width to bond spacing in a direction generally perpendicular to the edge 170 is calculated using the bond width A and the adjacent value of bond spacing C (as measured along a line perpendicular to the edge 170) which maximize the value A/C. For instance, in FIG. 12, the ratio of bond width A to bond spacing C is maximum along line 1004. Similarly, if the bond width B or the bond spacing D vary, the ratio of bond width to bond spacing in a direction generally parallel to the edge 170 is calculated using the bond width B and the adjacent bond spacing D (as measured along a line parallel to the edge 170) which maximize the value of B/D. For instance, in FIG. 12, the ratio of bond width B to bond spacing D is maximum along line 1002.

If the edge 170 is curved, the ratio of bond width to bond spacing in a direction generally perpendicular to the edge is calculated with the values of bond width A and bond spacing C which, when measured along a line perpendicular to a tangent to the edge 170, maximize the value of A/C. Similarly, the ratio of bond width to bond spacing in a direction generally parallel to the edge is calculated with the values of bond width B and bond spacing D which, when measured along a line parallel to a tangent to the edge 170, maximize the value of B/D.

In one preferred embodiment, the minimum spacing C between adjacent bonds in a direction generally perpendicular to the edge 170 is greater than the minimum spacing D between adjacent bonds in a direction generally parallel to the edge 170. The spacing C is preferably at least 1.25 times, and more preferably at least 1.5 times the spacing D. Such spacing is helps reduce the strength of the releasable seal 200 in a direction parallel to the edge 170 relative to the strength of the releasable seal 200 perpendicular to the edge 170. In addition, the minimum spacing C between adjacent bonds in a direction generally perpendicular to the edge 170 can be greater than the bond width A measured perpendicular to the edge 170, to further enhance peeling of the wrapper 160 in a direction parallel to the edge 170. In one embodiment the minimum spacing C can be at least 1.5 times the bond width A. In yet another embodiment of the present invention the bond width B measured generally parallel to the edge 170 can be greater than the bond width A measured generally perpendicular to the edge 170 to provide the desired ratios of bond width to bond spacing.

The releasable seal 200 should also have a relatively low bonded area ratio. The bonded area ratio is the maximum ratio of bonded area to unbonded area of the releasable seal 200, as measured in a sample area of the releasable seal 200. For a releasable seal 200 with a random pattern of discrete bonds 220, the sample area is a square having 0.5 centimeter sides. For a repeating pattern of discrete bonds 220, the sample area is a rectangle just large enough to enclose a repeating pattern of the discrete bonds 220. For the repeating array of discrete rectangular bonds 220 shown in FIG. 4, the sample area is a rectangle 207 connecting the centroids of four adjacent bonds 220, and the bonded area ratio is equal to the area of the bonds 220 enclosed within the rectangle 207 divided by the unbonded area within the rectangle 207, or $(A \times B)/((A+C) \times (B+D) - (A \times B))$. A relatively low bonded area ratio is desirable to provide a seal 200 that peels rather than tears, and to reduce the noise generated when the releasable seal 200 is opened. The bonded area ratio is less than 100 percent, preferably less than 50 percent, more preferably less than 20 percent, and even more preferably less than 10 percent.

FIGS. 8–10 show a die patterned impression surface 410 which can be used to make releasable seals 200 according to the present invention. The impression surface 410 comprises an array of protuberances in the shape of truncated pyramids 420. The array of truncated pyramids 420 extends in the machine direction (MD) and the cross machine direction (CD), as shown in FIG. 8. The array of pyramids 420 can comprise seven rows of pyramids, each row extending generally parallel to the cross machine direction, and 120 columns of pyramids 420, each column extending generally parallel to the machine direction. FIG. 8 shows portions of four rows and three columns of pyramids 420.

Each truncated pyramid 420 has four sides 422–425 and a top surface 430. The truncated pyramids 420 have an MD pitch (repeat spacing in the machine direction) designated 462 in FIG. 8, and a CD pitch (repeat spacing in the cross machine direction) designated 464. The top surface 430 has an MD width (width measured parallel to the machine direction) designated 452, and a CD width (width measured parallel to the cross machine direction) designated 454. Referring to FIGS. 9 and 10, the truncated pyramids 420 have a height 472 as viewed along a line generally parallel to the cross machine direction, and a height 482 as viewed along a line generally parallel to the machine direction. The sides 423 and 425 of adjacent pyramids 420 form an included angle designated 474 in FIG. 9, and the sides 422 and 424 of adjacent pyramids 420 form an included angle designated 484 in FIG. 10.

The MD pitch 462 of the pyramids 420 is preferably greater than their CD pitch 464. In particular, the difference between the MD pitch 462 and the MD width 452 of the top surface 430 is greater than the difference between the CD pitch 464 and the CD width 454. This arrangement is desirable to provide a ratio of bond width A to bond spacing C as measured in a direction generally perpendicular to the flexible wrapper edge 170 which is less than the ratio of bond width B to bond spacing D as measured parallel to the wrapper edge 170. As described above, this relationship of bond widths and bond spacings provides a releasable seal 200 having a strength parallel to the wrapper edge 170 which is reduced relative to the seal strength measured perpendicular to the wrapper edge 170.

Figure 11:
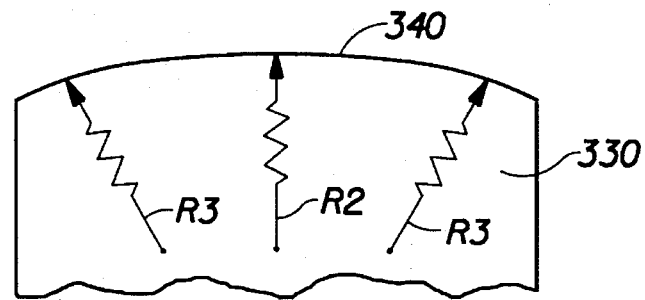
FIG. 11 is an end view of an anvil having a generally smooth surface with two radii of curvature.

The die impression surface 410 is preferably ground to have a radius R1 as shown in FIG. 7. Referring to FIG. 11, the generally smooth surface 340 of the anvil 330 is preferably machined to have a first radius R2, and a second radius R3 at each of the leading and trailing edges of the anvil surface 340. The second radius R3 helps to reduce the initial pressure applied to the wrapper 160 when the die 400 and the anvil 330 first engage the wrapper 160, thereby reducing variation from one row of bonds 220 to the next row of bonds 220. The radii R1 and R2 can be about 3.50 inches and the radius R3 can be about 3.0 inches.

The temperature controller of the sealing apparatus 300 should be set between about 250 to about 255 degrees Fahrenheit. The resulting temperature at the surface 340 of the anvil 330 should be between about 220 to about 240 degrees Fahrenheit, and the resulting temperature at the surface of the impression surface 410 of the die 400 should be between about 220 to about 240 degrees Fahrenheit. The sealing apparatus 300 should be operated to provide an interference of about 0.0035 inch at the interface of the surfaces 410 and 340, and a compressive load of about 500 pli (pounds per lineal inch of width of the surface 410 in the cross machine direction).

In one embodiment the MD pitch 462 is about 0.080 inch (2.0 mm) and the MD width 452 of the top surface 430 is about 0.019 inch (0.48 mm). The CD pitch 464 is about 0.050 inch (1.3 mm) and the CD width 454 is about 0.014 inch (0.35 mm). The heights 472 and 482 are about 0.017 inch (0.43 mm) and about 0.023 inch (0.58 mm), respectively. The included angles 474 and 484 are about ninety degrees each.

This arrangement provides discrete bonds 220 having a width A (corresponding to the MD width 452) of about 0.019 inch (0.48 mm) with a spacing C (corresponding to the difference of the MD pitch 462 and the MD width 452) of about 0.061 inch (1.5 mm), measured parallel to the wrapper edge 170. The spacing C is about 3 times the bond width A. The arrangement provides discrete bonds 220 with a width B (corresponding to the CD width 454) of about 0.014 inch (0.35 mm) and a spacing D (corresponding to the difference of the CD pitch 464 and the CD width 454) of about 0.036 inch (0.91 mm) measured parallel to the wrapper edge 170. The ratio of bond width to bond spacing perpendicular to the package edge 170 (0.019/0.061=0.31) is about 0.8 times the ratio of bond width to bond spacing parallel to the package edge 170 (0.014/0.036=0.39). The spacing between adjacent bonds 220 measured parallel to the edge 170 (0.061 inch) is about 1.7 times the spacing between adjacent bonds 220 measured perpendicular to the edge 170 (0.036 inch). The bonded area ratio is ((0.014)×(0.019))/((0.080)×(0.050)−(0.014)×(0.019)), or about seven percent.

This arrangement of discrete bonds 220 provides the advantage that the releasable seal 200 can have a first seal bond strength along a direction generally parallel to the edge 170 which is less than a second seal bond strength along a direction generally perpendicular to the edge 170. In particular, the arrangement can provide a releasable seal 200 where the second seal bond strength is at least about 1.1 times the first seal bond strength.

The bond strengths are measured using a constant rate of elongation tensile test machine such as an Instron Model 1122 tensile test machine available from the Instron Engineering Co. of Canton, Mass. The tensile test machine is operated at a cross head speed of twenty inches per minute. The bond strengths are measured in the portion of the releasable seal 200 joining all three of the panels 162, 164, and 166. The bond strengths should be calculated from an average of at least 10 measurements.

The first bond strength along a direction parallel to the edge 170 is measured using a rectangular sample of the releasable seal 200 cut from the wrapper 160, with a length of about 1.0 inch measured parallel to the edge 170 and a width of about 0.25 inch measured from, and perpendicular to, the edge 170. If a portion of the wrapper 160 extends intermediate the releasable seal 200 and the edge 170, such that the entire releasable seal 200 is positioned more than 0.25 inch from the edge 170 of the wrapper 160, the wrapper 160 should be trimmed to remove the unbonded wrapper material intermediate the edge 170 and the releasable seal 200. For instance, if the releasable seal 200 is spaced 0.25 inch or more from the edge 170 by unbonded portions of the wrapper panels extending intermediate the edge 170 and the releasable seal 200, the unbonded portions of the panels intermediate the edge 170 and the releasable seal 200 should be trimmed from the wrapper 160 by carefully cutting away those portions of the panels along a line parallel to the edge 170, thereby forming a new trimmed edge 170. As much of those portions of the panels as possible should be cut from the wrapper 160 without cutting into or otherwise damaging the releasable seal 200. The remaining width of the panels positioned intermediate the releasable seal 200 and the trimmed edge 170 should be no greater than the maximum bond spacing as measured perpendicular to the trimmed edge 170 (e.g. spacing C in FIG. 4). The sample width of about 0.25 inch is then measured from, and perpendicular to, the trimmed edge 170.

A portion of the panel 162 is separated from the panels 164 and 166 by peeling parallel to the edge 170, so that a portion of the panel 162 can be grasped in the moving jaw of the testing machine, and a portion of the panels 164 and 166 can be grasped together in the stationary jaw of the testing machine. The panels are mounted in the jaws widthwise so that as the jaws of the test machine move away from each other, the panel 162 is peeled away from the panels 164 and 166 in a direction parallel to the edge 170. The test machine records the force, in grams, as the panels are peeled apart. The first bond strength parallel to the edge 170 is obtained by dividing the maximum force (in grams) recorded by the test machine by the width of the sample of the releasable seal 200 in inches (about 0.25 inch). The first bond strength parallel to the edge 170 can be about 100 grams/inch for a releasable seal 200 having the arrangement of discrete bonds 220 described above, and formed in a wrapper comprising a 0.001 inch polyethylene film, with a sealing apparatus 300 using the operating temperature, loading, and interference listed above.

The second bond strength along a direction perpendicular to the edge 170 is measured using a sample of the releasable seal 200 cut from the wrapper 160, with a width of about 1.0 inch measured parallel to the edge 160 and a length of about 1.0 inch measured perpendicular to the edge 170. The length of the sample is long enough to include free portions of the panels 162, 164, and 166 (portions of the panels which are not bonded together by the releasable seal 200). The free portion of the panel 162 is grasped in the moving jaw of the test machine, and the free portions of the panels 164 and 166 are grasped in the stationary jaw of the test machine. The panels are mounted in the jaws widthwise so that as the jaws of the test machine move away from each other, the panel 162 is peeled away from the panels 164 and 166 in a direction perpendicular to the edge 170. The test machine records the force, in grams, as the panels are peeled apart. The second bond strength perpendicular to the edge 170 is obtained by dividing the maximum force (in grams) recorded by the test machine by the width of the sample of the releasable seal 200 in inches (about 1.0 inch). The second bond strength perpendicular to the edge 170 can be between about 110 grams/inch to about 140 grams/inch (or at least about 1.1 times the first bond strength) for a releasable seal 200 having the arrangement of discrete bonds 220 described above, and formed in a wrapper comprising a 0.001 inch polyethylene film, with a sealing apparatus 300 using the operating temperature, loading, and interference listed above.

The arrangement of bonds 220 described above provides a releasable seal 200 for a monolayer polyethylene film which is peelable parallel to the edge 170 and resists bursting during production operations. Such polyethylene films are desirable for use as wrappers for individually packaged sanitary napkins because they are relatively inexpensive and "quiet" (i.e. they do not generate excessive noise when deformed or when the releasable seal 200 is opened). The wrapper 160 is preferably formed of a film comprising at least 90 percent by weight polyethylene. High density polyethylene (HDPE), low density polyethylene (LDPE), and mixtures of HDPE and LDPE can be used. Suitable polyethylene films from which the wrapper 160 can be formed are commercially available from Tredegar Industries of Terre Haute, Ind. under the designations X9313 and X9353 cast films comprising about 60 percent HDPE and about 40 percent LDPE, and X9731 blown film.

In the arrangement of bonds described above, the bond width A is greater than the bond width B. In an alternative embodiment, the bond width A can be less than the bond width B to further increase ratio of bond width to bond spacing as measured perpendicular to the edge 170 relative to the ratio of bond width to bond spacing as measured parallel to the edge 170. For instance, the bond width A can be 0.014 inch, the bond width B can be 0.019 inch, and the bond spacings C and D can remain 0.061 and 0.036, respectively. A die impression surface 410 for forming such an array of discrete bonds could have a width dimension 452 of 0.014 inch, a width dimension 454 of 0.019 inch, and spacing dimensions 462 and 464 equal to 0.080 inch and 0.050 inch, respectively.

Figure 5:
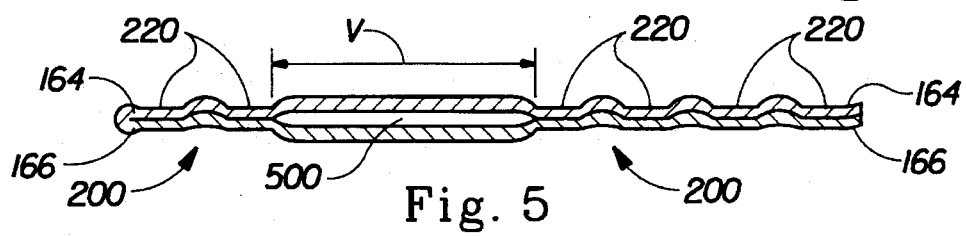
FIG. 5 is a cross-sectional schematic view taken along line 5—5 in FIG. 4 showing the vent passage in the releasable seal.

In one embodiment, the array of discrete bonds 220 can be interrupted by at least one vent passage 500, as shown in FIG. 4 and 5. The vent passage 500 extends through the releasable seal 200 to provide a flow path through which air in the interior of the flexible wrapper 160 can escape to the surrounding atmosphere. The vent passageway 500 helps reduce air pressure within the flexible wrapper 160 which could otherwise rupture the releasable seal 200. The vent passageway 500 in FIGS. 4 and 5 is positioned in the bottom portion of the flexible wrapper 160 adjacent the axis 153 (corresponding to the bottom right hand corner of the flexible wrapper 160 as viewed in FIG. 2), and extends between the panels 164 and 166. A second vent passageway 500 can be positioned in the bottom left hand corner (as viewed in FIG. 2) of the flexible wrapper 160. Similarly, a vent passage 500 can also be positioned in each of the top left and top right hand corners of the flexible wrapper 160 (as viewed in FIG. 2) adjacent the fold axis 152 to extend between the panels 162 and 164. Placement of the vent passages 500 in the corners of the flexible wrapper 160 helps to provide a flow path for air trapped between the panels at the fold axes 152 and 153.

Each vent passage 500 should be large enough to permit air to escape from the interior of the flexible wrapper 160, but be small enough to prevent dirt or other foreign objects from soiling the sanitary napkin 20 within the wrapper 160. The vent passage 500 preferably has a width V (FIGS. 4 and 5) which is greater than the maximum spacing between adjacent bonds 220. In one preferred embodiment the width V is at least two times, and more preferably at least four times the spacing between adjacent bonds 220 as measured in a direction generally parallel to the wrapper edge 170. The vent passage 500 preferably has a width V no more than about 0.25 inch to prevent dirt or other contaminants from entering the flexible wrapper 160 through the vent passage 500. The vent passage 500 can be formed in the releasable seal 200 by omitting (or grinding off) the appropriate number of columns of pyramids 420 on the impression surface 410 of the die 400 used to form the releasable seal 200.

The releasable seal 200 shown in FIG. 4 comprises an array of rows and columns of discrete bonds 220 having repeating bond widths and bond spacings parallel to and perpendicular to the edge 170. In other embodiments the releasable seal 200 can comprise other arrangements of bonds, such as a plurality of randomly sized and spaced bonds, or plurality of continuous or semi-continuous bonds. For instance, the seal 200 could comprise a plurality of continuous bonds arranged in a sinusoidal or lattice work configuration. In the preferred embodiment the releasable seal 200 comprises thermal-mechanical bonds. Thermal-mechanical bonding has the advantage that it can be economically used on high speed converting lines to provide releasable seals 200 having relatively consistent quality, and does not require the application of additional materials, such as adhesives.

While particular embodiments of the present invention have been illustrated and described, various changes and modifications can be made without departing from the spirit and scope of the present invention. The appended claims are intended to cover such changes and modifications that are within the scope of the current invention.

What is claimed is:

1. An individually packaged component comprising:
   a flexible wrapper, the flexible wrapper folded to have overlying wrapper portions extending intermediate a pair of spaced apart wrapper edges;
   a disposable absorbent article disposed intermediate the overlying portions of the flexible wrapper, the disposable absorbent article comprising a liquid pervious topsheet, a liquid impervious backsheet, and an absorbent core disposed intermediate the topsheet and the backsheet;
   wherein the folded wrapper comprises a releasable seal along each of the pair of spaced apart edges for joining the overlying portions of the wrapper; each releasable seal comprising an array of bonds, wherein the ratio of bond width to bond spacing in a direction generally perpendicular to the wrapper edge is less than the ratio of bond width to bond spacing in a direction generally parallel to the wrapper edge; and wherein the releasable seal has a bonded area ratio of no more than 50 percent.

2. The individually packaged component of claim 1 wherein each releasable seal comprises an array of discrete bonds.

3. The individually packaged component of claim 2 wherein each releasable seal comprises an array of discrete thermal-mechanical bonds.

4. The individually packaged component of claim 1 wherein the ratio of bond width to bond spacing in a direction generally perpendicular to the wrapper edge is less then 0.9 times the ratio of the bond width to bond spacing in a direction generally parallel to the wrapper edge.

5. The individually packaged component of claim 4 wherein the ratio of bond width to bond spacing in a direction generally perpendicular to the wrapper edge is less then 0.85 times the ratio of the bond width to bond spacing in a direction generally parallel to the wrapper edge.

6. The individually packaged component of claim 1 wherein the spacing between adjacent bonds in a direction generally perpendicular to the wrapper edge is greater than the spacing between adjacent bonds in a direction generally parallel to the wrapper edge.

7. The individually packaged component of claim 6 wherein the spacing between adjacent bonds in a direction generally perpendicular to the wrapper edge is at least 1.25 times the spacing between adjacent bonds in a direction generally parallel to the wrapper edge.

8. The individually packaged component of claim 7 wherein the spacing between adjacent bonds in a direction generally perpendicular to the wrapper edge is at least 1.5 times the spacing between adjacent bonds in a direction generally parallel to the wrapper edge.

9. The individually packaged component of claim 1 wherein the spacing between adjacent bonds in a direction generally perpendicular to the wrapper edge is greater than the bond width measured perpendicular to the wrapper edge.

10. The individually packaged component of claim 1 wherein the releasable seal has a bonded area ratio of no more than twenty percent.

11. The individually packaged component of claim 10 wherein the releasable seal has a bonded area ratio of no more than ten percent.

12. The individually packaged component of claim 1 wherein the releasable seal has a first seal bond strength along a direction generally parallel to the wrapper edge which is less than a second seal bond strength along a direction generally perpendicular to the wrapper edge.

13. The individually packaged component of claim 12 wherein the second seal bond strength is at least about 1.1 times the first seal bond strength.

14. The individually packaged component of claim 1 wherein the releasable seal comprises a plurality of rows of discrete bonds, each row extending generally parallel to the wrapper edge, and a plurality of columns of discrete bonds, each column extending generally perpendicular to the wrapper edge.

15. The individually packaged component of claim 14 wherein the array of discrete bonds is interrupted by at least one vent passage having a width greater than the maximum spacing between adjacent bonds.

16. The individually packaged component of claim 15 wherein each vent passage has a width at least four times the spacing between adjacent bonds in a direction generally parallel to the wrapper edge.

17. An individually packaged component comprising:
a disposable absorbent article comprising a liquid pervious topsheet, a liquid impervious backsheet, and an absorbent core disposed intermediate the top sheet and the backsheet;

a flexible wrapper, the flexible wrapper having a pair of spaced apart edges;

wherein the absorbent article and the wrapper are folded as a unit about at least two spaced apart fold axes, at least a portion of the disposable absorbent article disposed between a first panel and a second panel of the folded wrapper, and a third panel of the folded wrapper forming a closure flap;

wherein the folded wrapper comprises a releasable seal along each of the pair of spaced apart edges for joining at least two of the wrapper panels; each releasable seal comprising an array of discrete thermal-mechanical bonds, wherein the ratio of bond width to bond spacing in a direction generally perpendicular to the wrapper edge is less than the ratio of bond width to bond spacing in a direction generally parallel to the wrapper edge; and wherein the releasable seal has a bonded area ratio of no more than 50 percent.

18. The individually packaged component of claim 17 wherein each releasable seal has a bonded area ratio of no more than twenty percent.

19. The individually packaged component of claim 17 wherein each releasable seal comprises a plurality of rows of discrete bonds, each row extending generally parallel to a wrapper edge, and a plurality of columns of discrete bonds, each column extending generally perpendicular to the wrapper edge.

20. The individually packaged component of claim 19 wherein the spacing between adjacent rows is greater than the spacing between adjacent columns.

21. The individually packaged component of claim 17 wherein the array of discrete bonds is interrupted by at least one vent passage having a width greater than the maximum spacing between adjacent bonds.

22. The individually packaged component of claim 17 wherein the releasable seal has a first seal bond strength along a direction generally parallel to a wrapper edge which is less than a second seal bond strength along a direction generally perpendicular to the wrapper edge.

23. The flexible package of claim 22 wherein the second seal bond strength is at least 1.1 times the first seal bond strength.

24. An individually packaged component comprising:
a disposable absorbent article comprising a liquid pervious topsheet, a liquid impervious backsheet, and an absorbent core disposed intermediate the topsheet and the backsheet;

a flexible wrapper, the flexible wrapper having a pair of spaced apart edges;

wherein the absorbent article and the wrapper are folded as a unit about at least two spaced apart fold axes, at least a portion of the disposable absorbent article disposed between a first panel and a second panel of the folded wrapper, and a third panel of the folded wrapper forming a closure flap; and wherein the folded wrapper comprises a releasable seal along each of the pair of spaced apart wrapper edges for joining at least two of the wrapper panels; each releasable seal comprising an array of discrete thermal-mechanical bonds, the array of discrete bonds comprising a plurality of rows of discrete bonds, each row extending generally parallel to the wrapper edge, and a plurality of columns of discrete bonds, each column extending generally perpendicular to the wrapper edge; and wherein the spacing between adjacent rows is greater than the spacing between adjacent columns.

25. The flexible package of claim 24 wherein the spacing between adjacent rows is greater than the bond width measured perpendicular to the wrapper edge.

26. A flexible package comprising a plurality of thermoplastic film layers joined at a releasable seal along at least one edge of the package, the releasable seal comprising an array of discrete bonds joining the layers, wherein the array comprises a plurality of rows of discrete bonds, each row extending generally parallel to the package edge, and a plurality of columns of discrete bonds, each column extending generally perpendicular to the package edge, wherein the ratio of bond width to bond spacing in a direction generally perpendicular to the package edge is less than the ratio of bond width to bond spacing in a direction generally parallel to the package edge, and wherein the spacing between adjacent rows is greater than the spacing between adjacent columns.

* * * * *

UNITED STATES PATENT AND TRADEMARK OFFICE
CERTIFICATE OF CORRECTION

PATENT NO. : 5,462,166
DATED : October 31, 1995
INVENTOR(S) : Gerald T. Minton et al.

It is certified that error appears in the above-indentified patent and that said Letters Patent is hereby corrected as shown below:

Column 12, line 13    delete "comers" and insert --corners--.

Signed and Sealed this

First Day of July, 1997

Attest:

BRUCE LEHMAN

*Attesting Officer*    *Commissioner of Patents and Trademarks*